US011564765B2

(12) United States Patent
Richart et al.

(10) Patent No.: US 11,564,765 B2
(45) Date of Patent: Jan. 31, 2023

(54) MEDICAL ASSEMBLY COMPRISING A MEDICAL ARTICLE AND A PACKAGE CONTAINING SAID ARTICLE

(71) Applicant: DEPUY SYNTHES PRODUCTS, INC., Raynham, MA (US)

(72) Inventors: Olivier Richart, Lagord (FR); Gregoire Larche, Cholet (FR); Jean-Pierre Podgorski, Saint Crespin sur Moine (FR)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 17/519,991

(22) Filed: Nov. 5, 2021

(65) Prior Publication Data

US 2022/0054215 A1  Feb. 24, 2022
US 2022/0257328 A9  Aug. 18, 2022

Related U.S. Application Data

(63) Continuation of application No. 16/563,433, filed on Sep. 6, 2019, now Pat. No. 11,166,780, which is a
(Continued)

(30) Foreign Application Priority Data

Apr. 27, 2010 (FR) ...................................... 1053191
Apr. 22, 2011 (FR) ...................................... 1153520

(51) Int. Cl.
*B65D 81/32* (2006.01)
*A61B 50/30* (2016.01)
(Continued)

(52) U.S. Cl.
CPC ............ *A61B 50/30* (2016.02); *A61B 17/865* (2013.01); *A61F 2/0095* (2013.01);
(Continued)

(58) Field of Classification Search
CPC ... A61C 8/0087; A61B 17/865; A61F 2/0095; B65D 77/0486; B65D 51/002
(Continued)

(56) References Cited

U.S. PATENT DOCUMENTS 4,712,681 A  12/1987 Branemark et al.
4,856,648 A  8/1989 Krueger
(Continued)

FOREIGN PATENT DOCUMENTS

DE  10146905  7/2003
EP  1523955 A1  4/2005
(Continued)

OTHER PUBLICATIONS

International Search Report dated Oct. 19, 2011.
(Continued)

*Primary Examiner* — Ernesto A Grano
(74) *Attorney, Agent, or Firm* — Kramer & Amado, P.C.

(57) ABSTRACT

A medical package containing a medical article, including: a support element comprising a hollow support tube and a support cap, wherein the support element includes a first chamber configured to enclose the medical article and wherein the support cap includes a support structure configured to hold the medical article captive; a stopper configured to be coupled to the hollow support tube in such a way that the support element has a grip part that protrudes from the stopper, the grip part of the support element configured to be held by a hand of a person; a hollow protective cover configured to be coupled to the stopper in such a way as to delimit, in cooperation with the stopper, a second chamber inside which there extends the grip part of the support element, the hollow protective cover configured to be separated from the stopper, wherein when the hollow protective cover is coupled to the stopper, a part of the
(Continued)

stopper protrudes from the hollow protective cover, and is configured to form a grip end of the stopper that is configured to be held by a hand of a person, when the hollow protective cover is separated from the stopper, wherein a part of the support element is configured to be engaged by force inside the stopper, and when the hollow protective cover is separated from the stopper, the support element remains coupled to the stopper while the support element is also separable from the stopper when a person holds the grip part of the support element and pulls the support element so as to separate it from the stopper.

30 Claims, 7 Drawing Sheets

Related U.S. Application Data continuation of application No. 16/445,890, filed on Jun. 19, 2019, now Pat. No. 11,166,779, which is a continuation of application No. 14/112,355, filed as application No. PCT/FR2012/050852 on Apr. 19, 2012, now Pat. No. 10,327,857, and a continuation-in-part of application No. 13/583,801, filed as application No. PCT/FR2011/050943 on Apr. 22, 2011, now Pat. No. 9,265,579.

(51) Int. Cl.
*A61F 2/00* (2006.01)
*B65D 77/04* (2006.01)
*A61B 17/86* (2006.01)
*A61B 50/00* (2016.01)

(52) U.S. Cl.
CPC .. B65D 77/0493 (2013.01); *A61B 2050/0054* (2016.02); *A61B 2050/0064* (2016.02); *A61B 2050/0066* (2016.02); *A61B 2050/3006* (2016.02)

(58) Field of Classification Search
USPC ........................................................ 206/438
See application file for complete search history.

(56) References Cited

U.S. PATENT DOCUMENTS

| | | |
|---|---|---|
| 5,062,800 A | 11/1991 | Niznick |
| 5,332,443 A | 7/1994 | Chew et al. |
| 5,437,550 A | 8/1995 | Beaty et al. |
| 5,538,428 A | 7/1996 | Staubli |
| 5,558,230 A | 9/1996 | Fischer et al. |
| 5,600,608 A | 2/1997 | Weiss et al. |
| 5,622,500 A | 4/1997 | Niznick et al. |
| 5,692,904 A | 12/1997 | Beaty et al. |
| 5,755,575 A | 5/1998 | Biggs |
| 6,108,274 A | 8/2000 | Pearce |
| 6,145,685 A | 11/2000 | Dick |
| 6,203,323 B1 | 3/2001 | Beaty et al. |
| 6,217,332 B1 | 4/2001 | Kumar |
| 6,247,932 B1 | 6/2001 | Sutter |
| 6,280,192 B1 | 8/2001 | Groll et al. |
| 6,287,117 B1 | 9/2001 | Niznick |
| 6,483,775 B1 | 11/2002 | Spackman et al. |
| 6,561,805 B2 | 5/2003 | Kumar |
| 6,853,604 B2 | 2/2005 | Spackman et al. |
| 7,120,087 B2 | 10/2006 | Lee et al. |
| 7,451,870 B2 | 11/2008 | Donahoe |
| 7,854,316 B2 | 12/2010 | Park et al. |
| 7,921,991 B2 | 4/2011 | Sato et al. |
| 8,083,054 B2 | 12/2011 | Nihei et al. |
| 8,181,773 B2 | 5/2012 | Guenter et al. |
| 8,413,811 B1 | 4/2013 | Arendt |
| 2003/0221977 A1 | 12/2003 | Kumar et al. |
| 2005/0023166 A1 | 2/2005 | Howlett et al. |
| 2005/0098460 A1 | 5/2005 | Smith et al. |
| 2009/0065387 A1 | 3/2009 | Bammerlin et al. |
| 2012/0318697 A1 | 12/2012 | Stern |

FOREIGN PATENT DOCUMENTS

| | | |
|---|---|---|
| FR | 2581867 A1 | 11/1986 |
| WO | 0002496 | 1/2000 |

OTHER PUBLICATIONS

Search Report dated Jul. 13, 2015.
International Search Report, dated Mar. 4, 2013, from corresponding PCT application.

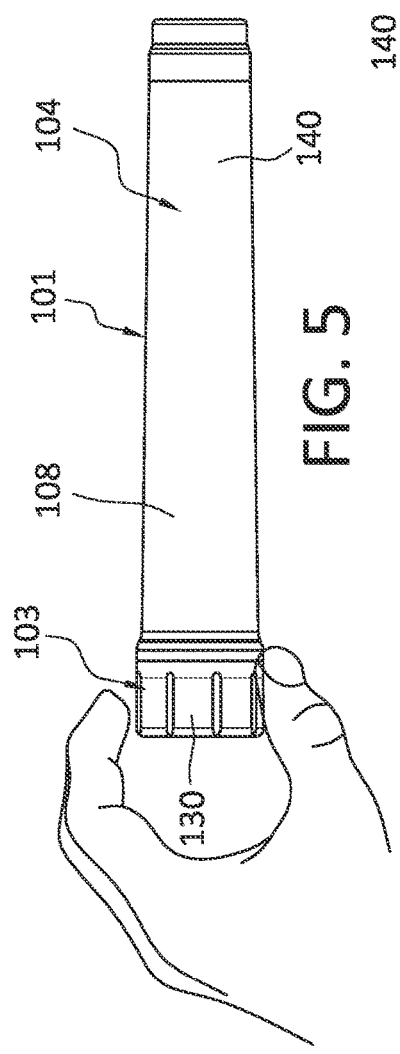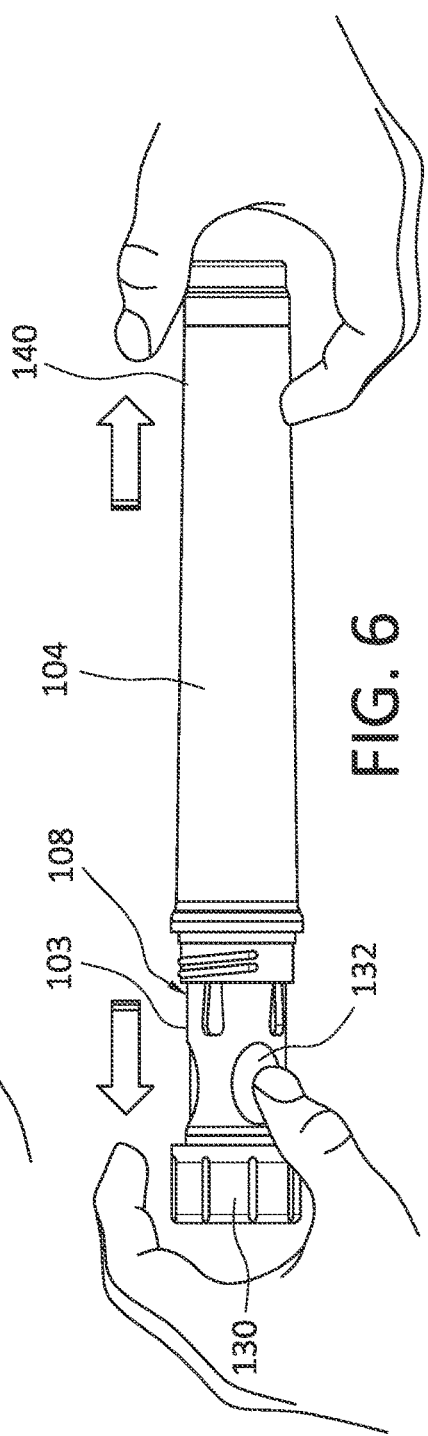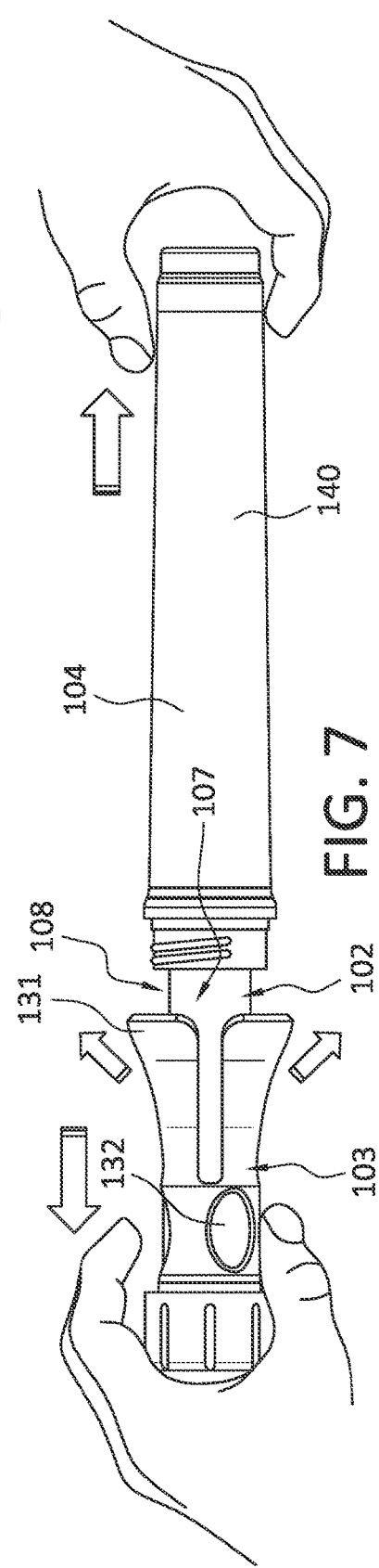

MEDICAL ASSEMBLY COMPRISING A MEDICAL ARTICLE AND A PACKAGE CONTAINING SAID ARTICLE

RELATED APPLICATIONS

This application is a continuation of U.S. Ser. No. 16/563,433, filed Sep. 6, 2019, which is a continuation of U.S. Ser. No. 16/445,890, filed Jun. 19, 2019 which application is a continuation of U.S. Ser. No. 14/112,355, filed Oct. 31, 2013, which is a National Stage of International Application No. PCT/FR2012/050852, filed Apr. 19, 2012 and a Continuation-In-Part of U.S. application Ser. No. 13/583,801 filed Sep. 10, 2012, now U.S. Pat. No. 9,265,579, which is a National Stage of International Application No. PCT/FR2011/050943, filed Apr. 22, 2011, the entire contents of each of which are incorporated herein by reference for all purposes as if fully set forth herein. This application is based upon and claims the benefit of priority from prior French Patent Application Nos. 1153520, filed Apr. 22, 2011 and 1053191, filed Apr. 27, 2010, which each are hereby incorporated by reference for all purposes as if fully set forth herein.

FIELD OF THE INVENTION

The present invention generally relates to packages for objects, in particular for medical components that are preferably sterilized. The invention relates more particularly to a medical assembly, preferably a sterilized one, comprising a medical article and a package containing said article.

BACKGROUND

In the prior art, packages are known that are in the form of plastic blister shells or bags in which an object is contained. For medical components that must be unpackaged in near-aseptic conditions, such packages pose problems of contamination while the package is being passed from one person to another and while said package is being opened. Specifically, from its departure from a "dirty" work zone, i.e. without special aseptic conditions, to its arrival in a "clean" work zone, i.e. a work zone in which given aseptic conditions are maintained, e.g. the zone of an operating block, the package that arrives in the clean zone is contaminated on the outside, and this presents a risk of the medical object being contaminated while it is being removed from said package.

In order to limit the risk of contamination, it is known to open the bag in such a manner as to cause the object to fall onto a worktop without any need to touch said object. Only a sterile assistant or surgeon picks up the object. However, a solid object runs the risk not only of being damaged on impact with the worktop, or even of rolling onto the floor, but also of being contaminated by foreign bodies present on the worktop.

Document U.S. Pat. No. 5,062,800 describes a medical package for a dental implant that includes a support element provided with fastener means for fastening the implant, and a stopper that can be coupled to the support element in such a manner that the support element projects from said stopper. Said package also includes a cover that covers the stopper. However, the cover completely covers the length of the stopper such that the operator has no option other than to empty the content of the cover by causing said content to fall onto a worktop. As mentioned above, causing the implant to fall may damage it and increases the risk of contamination.

In the prior art, packages are known that are in the form of external and internal double envelopes of the sachet type, or in the form of double plastic blister shells, or a combination of both, in which an article is contained. In the case of medical components that have to be unpacked in near-aseptic conditions, such packages may pose problems of contamination when the package is passed from one person to another and when said package is being opened.

Specifically, from its departure from a work area referred to as dirty, that is to say without any special aseptic conditions, to its arrival in a work area referred to as clean, that is to say a work area in which given aseptic conditions are maintained, for example the "sterile" area of an operating theater, the package arriving in the clean area is contaminated on its outer envelope, which poses a risk of the medical component being contaminated when it is removed from said package.

In order to limit the risk of contamination of the article contained in the package, it is known to open said package in such a way as to cause the article to fall onto a work surface, so as not to have to touch said article. Only the surgeon or a sterile assistant picks up the article. However, the article runs the risk not only of being damaged on impact with the work surface, in the case of a solid article, or even of rolling onto the floor, but also of being contaminated by foreign bodies present on the work surface. It also happens that the operator passes the external envelope of the package to the sterile assistant, who then has to try to take hold of the internal envelope without incurring asepsis. However, there is a very great risk of the assistant touching a contaminated area of the package during this operation, and of the article taken hold of in turn being contaminated.

In addition, in document U.S. Pat. No. 5,062,800, the implant is fixed to the corresponding support element of the package. This means that the operator has to perform a specific maneuver in order to remove the implant from the support element once the other elements have been withdrawn, which complicates the intervention by the operator and does not allow him to quickly take hold of the implant that he requires. In particular, in the field of emergency surgery or traumatology, the operator who requires said implant must be able to access it as quickly as possible, while of course limiting the risk of contamination of said implant.

SUMMARY OF THE INVENTION

An object of the present invention is to propose a package for packaging and unpackaging an object, which package makes it possible to limit the risks of contamination of the object, while making it possible to unpackage the object without having to let get of it or touch it directly.

To this end, the invention provides a package for an object such as a preferably-sterilized medical component, said package being characterized in that it comprises:
  a support element provided with means for coupling said object to said support element;
  a first hollow protective element, referred to as a stopper, that can be coupled to the support element of said object, preferably by interfitting with partial overlap, such that the support element presents a portion, referred to as a "grip portion", that projects from said stopper;
  said support element, alone or in co-operation with the stopper, defining a first chamber containing said object; and
  a second hollow protective element, referred to as a cover;

said package being further characterized in that said cover can be coupled to the stopper, preferably by interfitting with partial overlap, so as to co-operate with said stopper to define a second chamber inside which said grip portion of the support element extends; and in that, while the cover is coupled to the stopper, a portion, referred to as a "grip portion", of the stopper projects from the cover.

By means of the grip portions of each of the protective elements and of the support element, which support element projects from the protective element to which it is coupled, the chambers defined by interfitting said elements, with partial overlap, can be opened until the object can be accessed, without ever letting go of or touching said object, and with a reduced risk of the object being contaminated.

Specifically, while the package is being passed from a first operator to a second operator, the protective cover may be removed in such a manner as to open the first chamber so as to uncover the grip end of the support element of the object and retain, for the second operator, only the sub-assembly formed of the stopper and of the support element.

Since the second operator holds said sub-assembly by the end of the stopper remote from the support element, the end of the support element uncovered by opening the first chamber is clean and may be offered to the last operator, e.g. the surgeon. The last operator is the operator who takes hold of the object by means of an instrument in order to use it.

Naturally, the first operator and the second operator may be a single operator who removes the cover from the stopper by taking hold of the cover with one hand and the stopper with the other, so as to uncover the support element.

The stopper and the support element may thus be separated in such a manner as to open the chamber containing the object that remains coupled to the support element held by the last operator. The last operator who thus retains only the support element to which the object is coupled can use the clean hand that holds the grip end of the support element to deactivate the coupler means, and can use the other hand, which is also clean, to take hold of the object, e.g. by means of an instrument.

Such a design of the package of the invention makes it possible to make a package with a small number of parts, mainly three, so that while the package is being passed from a dirty zone to a clean zone via various people, neither the support element nor the object are touched by a person in the dirty zone, and the object coupled to the support element is never let go. The risk of contamination is thus very greatly reduced.

According to an advantageous characteristic of the invention, the stopper and the cover are each formed by a respective elongate hollow body that is open at one end and closed at the other end.

The elongate nature of the object-protecting elements formed by the cover and the stopper, makes it possible to benefit from a safety distance while the chambers are being opened and the various portions of the package are being passed from one person to another. Specifically, two people may take hold of the outside of the package formed by the stopper and the cover, or of the sub-assembly of the package formed by the stopper and the support element, each holding a respective opposite end, thereby reducing the risk of contamination.

According to an advantageous characteristic of the invention, the means for coupling the object to the support element comprise a deformable body, referred to as a valve, presenting an orifice, preferably of oval shape, that is capable of passing, by deformation of said body, from a "retaining" configuration in which said orifice of the valve presents a shape and/or dimensions making it possible to clamp the object, to a "releasing" configuration in which said orifice presents a shape and/or dimensions making it possible to release said object relative to said orifice of the valve.

In another particular embodiment of the coupler means, of the type for which said object presents an elongate body, said means for coupling the object to the support element include a deformable elongate body, referred to as a mandrel, along and inside which an orifice is formed for inserting the object. Said means also include a bellows that surrounds the mandrel and that is capable of passing from a deployed position of the folds of the bellows, in which said bellows bears against the mandrel in such a manner as to clamp the insertion orifice around the object, to a compressed position of said folds of the bellows, in which the bellows does not press against the mandrel so as to enable the object to move relative to said insertion orifice for inserting the mandrel.

Preferably, said support element includes at least two arms that are spaced apart from each other and that extend on either side and along the assembly formed of the mandrel and of the bellows.

In another particular embodiment of the coupler means, the means for coupling the object to the support element present a configuration for holding the object captive in a given orientation of said object, and a configuration for releasing said object by pivoting it.

In another particular embodiment of the coupler means, the support element and the means for coupling the object to the support element are configured to hold the object suspended through said coupler means, in such a manner as to make it possible to see the length of said object while said object is coupled to the support element.

According to an advantageous characteristic of the invention, said support and protective elements of the package are interfitted, with partial overlap, by friction and/or by screw-fastening.

In a particular embodiment of said package for which said support element alone defines said first chamber containing said object, and said support element is formed of at least two parts that can be coupled and uncoupled relative to each other, preferably by interfitting with partial overlap, so as to form said first chamber containing said object.

In another particular embodiment of said package for which said support element co-operates with the stopper to define said first chamber containing said object, said support element defines an open cavity that is to be closed by the stopper.

Preferably, said stopper, and possibly the cover, present(s) at least one predefined location for positioning at least one finger of a person.

Advantageously, the support element and/or the stopper and/or the cover present(s) a portion, preferably formed by a membrane, that is impermeable to bacteria but permeable to gas so as to enable said first chamber and/or said second chamber to be sterilized with gas.

The invention also relates to a method of unpackaging a preferably-sterilized medical object contained in a package as described above, said method being characterized in that it comprises the following steps:

a) a first person separating the cover from the stopper in such a manner as to uncover the support element;

b) a second person distinct from said first person taking hold of the support element; and c) separating said support element from the stopper while the stopper is being held by the first person.

Naturally, provision may be made for the cover and the stopper to be separated by two different people in a dirty zone, instead of by a single person, with one holding one end of the stopper and the other holding one end of the cover.

Advantageously, said method comprises the following additional steps:
d) optionally putting said support element that closes the object on standby in a standby zone, while said object is waiting to be used; and
e) opening the first chamber defined by said support element in order to remove said object.

The invention also relates to an assembly comprising an object such as a preferably-sterilized medical component and a package as described above containing said object coupled to said support element.

Preferably, said object presents an end for gripping, e.g. by an instrument, said object being coupled to the support element in such a manner that its grip end is free and points away from the grip portion of the support element.

The object of the present invention is to make available a package for the packing and unpacking of an article, which package makes it possible to limit the risks of contamination of the article while at the same time permitting easy and quick access to said article.

To this end, the invention relates to a medical assembly, preferably a sterilized one, comprising a medical article and a package containing said article, said package comprising a hollow support element inside which said article is free, characterized in that said package comprises: a first protective element, called a stopper, which can be coupled to the support element of said article, preferably by engagement with partial overlap, in such a way that the support element has a grip part that protrudes from said stopper, said support element delimiting on its own, or in cooperation with the stopper, a first chamber that encloses said article, a second hollow protective element, called a cover, said cover being able to be coupled to the stopper, preferably by engagement with partial overlap, in such a way as to delimit, in cooperation with said stopper, a second chamber inside which there extends the grip part of the support element, and in that, in the state when the cover is coupled to the stopper, a part of the stopper protrudes from the cover.

By virtue of the grip part of each protective element and of the support element, which protrudes from the protective element to which it is coupled, the chambers defined by engagement of said elements, with partial overlap, can be opened in order to access the article without ever letting go of or touching said article and with a reduced risk of contamination of the article.

Indeed, when the package is passed from a first person, whose hands are presumed to be "contaminated", to a second person, whose hands are presumed to be "clean", the protective cover can be withdrawn by the first person in such a way as to open the "second" chamber in order to uncover the grip end of the support element of the article and retain, for the second person, only the sub-assembly composed of the stopper and of the support element.

The first person holds said sub-assembly via the end of the stopper remote from the support element and can offer the second person, for example the surgeon, the clean end of the support element, uncovered by the opening of the first chamber.

The stopper and the support element can then be separated in such a way as to open the chamber containing the article. The second person, who thus retains only the support element containing the article, can thus hold the grip end of the support element in his clean hand while taking hold of the article, for example, via his other clean hand.

Such a design of the package according to the invention makes it possible to produce a package with a smaller number of component parts, basically three, in such a way that, when the package is passed from a dirty area to a clean area by way of different persons, neither the support element nor the article are touched by anyone in the dirty area, and the article contained in the support element is never let go of. The risk of contamination is thus very considerably reduced.

In addition, the fact that the article is free inside the support element allows easy and quick access to the article. In particular, in the field of emergency surgery, the person who requires said article must be able to quickly access said article while at the same time limiting the risk of contamination of said article, as is explained in detail below.

According to an advantageous feature of the invention, said stopper comprises a peripheral wall called an internal wall, and a peripheral wall called an external wall which surrounds said internal peripheral wall with clearance in order to define, between said peripheral walls, an annular space for engagement of that part of the cover intended to be coupled to said stopper, the internal peripheral wall defining a space for engagement of that part of the support element intended to be coupled to said stopper.

According to an advantageous feature of the invention, the internal face of the internal peripheral wall of the stopper is provided with retaining means for retaining that part of the support element engaged inside the space delimited by said internal peripheral wall of the stopper.

According to an advantageous feature of the invention, said retaining means comprise lugs which are intended to be in bearing contact with the support element in the state when said support element is engaged in the stopper, and the lugs are distributed on the internal peripheral face of the stopper, about the axis of said stopper, by being spaced apart at angles from one another.

According to an advantageous feature of the invention, each lug comprises a ramp forming part, directed toward the axis of the stopper starting from a bottom point of the ramp situated at the open end of the stopper to a top point of said ramp situated at the closed end of said stopper, in such a way that, when the support element is engaged inside the space defined by the internal peripheral wall of the stopper, said support element, by bearing on said ramp, pushes said lug radially and deforms the corresponding internal peripheral wall toward the external peripheral wall.

According to an advantageous feature of the invention, the lugs form spacers for maintaining a radial distance between the support element and the internal peripheral wall of the stopper, the spacing between the lugs defining a space for fluid communication between the inside of the peripheral wall of the stopper and the inside of the cover.

According to an advantageous feature of the invention, said external and/or internal peripheral walls of the stopper comprise screwing means for cooperating with complementary screwing means formed on the cover.

According to an advantageous feature of the invention, the internal face of the external peripheral wall of the stopper has a tapping that is able to cooperate with a thread formed on the external face of the peripheral wall of the cover.

According to an advantageous feature of the invention, when said support element delimits on its own said first chamber enclosing said article, said support element is formed by at least two components that can be coupled to/uncoupled from each other, preferably by engagement with partial overlap, in order to form said first chamber enclosing said article.

Thus, the design of the package in the form of a support element coupled to a stopper which delimits, in cooperation with a cover, a chamber in which part of the support element protrudes from the stopper, allows the support element to be passed from a first person to a second person without the first person touching the support element and with a reduced risk of contamination between the first person and the second person, such that the support element enclosing said article arrives at the clean area with a reduced risk of contamination. In addition, the design of the support element in the form of two component parts, which can be coupled in order to delimit a closed cavity (first chamber), makes it possible to protect said article pending its use.

According to an advantageous feature of the invention, when said support element delimits, in cooperation with the stopper, said first chamber enclosing said article, said support element delimits an open cavity intended to be closed by said stopper.

According to such an embodiment, said package can be composed of only three component parts, namely the cover, the stopper, and the support element. Each component part is in the form of a hollow body that is open in the manner of a test tube. Thus, the support element can be coupled to the stopper in order to delimit the first chamber which encloses said article, and the stopper can be coupled to the cover in order to delimit the second chamber which encloses that part of the support element protruding from the stopper.

According to an advantageous feature of the invention, the stopper and the cover are each formed by an elongate hollow body that is open at one end and closed at the other end.

The elongate character of the one or more elements which protect the article, and which are formed by the cover and the stopper, provides the benefit of a safety distance when the chambers are opened while passing the various parts of the package from one person to another.

According to an advantageous feature of the invention, said stopper, and if appropriate the cover, has (have) predefined locations permitting the positioning of at least two fingers, preferably three fingers, of a person in order to allow him to grip said stopper, and if appropriate said cover, in the area of said predefined locations.

Advantageously, said stopper, and if appropriate said cover, has (have) predefined locations permitting the positioning of at least three fingers in order to grip between them said stopper, and if appropriate said cover.

A predefined location of this kind makes it possible to limit the risk of contamination of the support element and therefore of the article contained in said support element.

According to an advantageous feature of the invention, when said cover can be coupled to the stopper by engagement with partial overlap, said stopper has at least one deformable part, preferably at least one deformable wing, which is configured such that, on the one hand, when said deformable part of the stopper is covered by the cover, said part comes to bear against the internal face of the cover in order to allow the stopper to be coupled to the cover by friction, and, on the other hand, such that said part is able to deform in order to permit the separation of the cover from the stopper.

Such a deformable part of the stopper ensures good leak tightness between the stopper and the cover in the coupled state of these two component parts.

According to an advantageous feature of the invention, said support element and protective elements of the package engage each other, with partial overlap, by friction and/or by screwing.

According to an advantageous feature of the invention, the support element and/or the stopper and/or the cover have a part, preferably formed by a membrane, that is impermeable to bacteria but permeable to gases in order to permit gas sterilization of said first chamber and/or of said second chamber.

The invention also relates to a method of unpacking a medical article contained in a package of a medical assembly, preferably a sterilized one, as has been described above, characterized in that said method comprises the following steps:
 a) separation of the cover from the stopper by a first person, referred to as the contaminated person, in order to uncover the support element,
 b) gripping of the support element by a second person, referred to as the non-contaminated person,
 c) separation of said support element from the stopper held by said contaminated person.

According to an advantageous feature of the invention, said method comprises
The following additional steps:
 d) optionally keeping said support element, which encloses the article, in a stand-by area pending the use of said article,
 e) opening the first chamber defined by said support element in order to remove said article therefrom.

These method steps apply in particular to an embodiment of the package according to the invention in which the support element on its own forms said first chamber, and in which said support element is composed of at least two component parts which can be coupled to/uncoupled from each other and which, in the coupled state, delimit a closed cavity forming said first chamber. The first person offers the second person the remaining package composed of the stopper and of the support element, by presenting to him the end of said remaining package formed by said support element. The second person then pulls said support element in such a way as to separate it from said stopper. The support element, which forms a cavity enclosing the article, can then be placed on a table in a decontaminated area pending its use. The embodiment of the support element in the form of a cavity enclosing the article makes it possible to protect said article, which remains inside the support element pending its use, against external contamination. It then suffices for the second person, or another "clean" person, to open the first chamber formed by said support element, by separating at least the two component parts that form said support element.

According to an advantageous feature of the invention, said method comprises, between steps a) and b), the following additional step in which the first person offers the second person the remaining package composed of the stopper and of the support element, by presenting to him the end of said remaining package formed by said support element, orienting said remaining package in such a way that the support element is at a height lower than that of the stopper, such that said article remains contained in the support element during the separation of said support element from the stopper, so as to avoid said article falling to the ground.

This method step applies in particular to an embodiment of the package according to the invention in which the support element forms said first chamber in cooperation with the stopper, and in which said support element is in the form of an elongate hollow body that is open at one end and closed at the other end and is able to contain said article. The first person, referred to as "contaminated", offers the second person, referred to as "clean" or "sterile", the remaining package composed of the stopper and of the support element, by presenting to him the end of said remaining package formed by said support element, orienting said remaining package in such a way that the support element is at a height lower than that of the stopper, such that said article remains contained in the support element during the separation of said support element from the stopper, so as to avoid said article falling to the ground. The second person, or another clean person, is then able, if appropriate with the aid of a tool, to take hold of the article in contact with said support element.

BRIEF DESCRIPTION OF THE DRAWINGS

The invention can be well understood on reading the following description of embodiments, with reference to the accompanying drawings, in which:

FIG. 5 is a view of a package according to the invention in a first embodiment, inside which a medical component is packed;

FIGS. 6 to 8 are views of the package from FIG. 5 during a first unpacking step in which the cover is withdrawn by a first person, called the contaminated person, the remaining sub-assembly composed of the stopper and of the support element being held via the stopper by the hand of the contaminated person;

DETAILED DESCRIPTION

Figure 2:
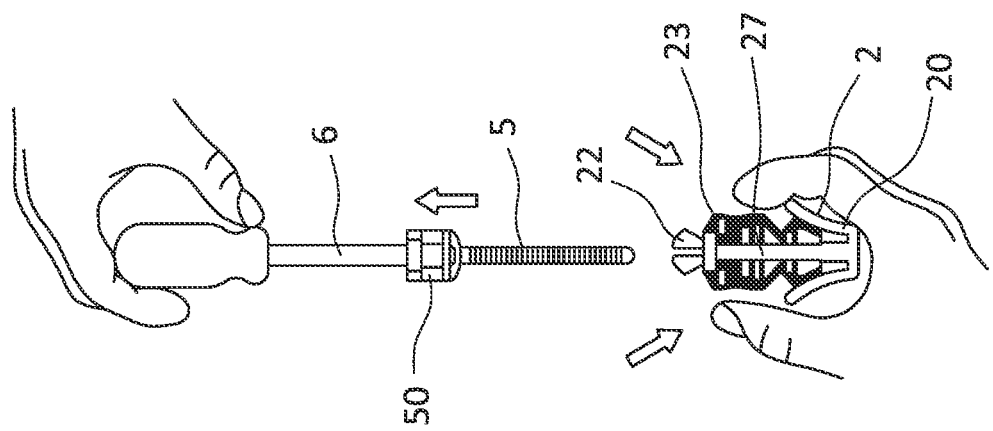
FIG. 2 is a section view of the support element in a second embodiment of the package in which the coupler means for coupling the medical component to the support element are formed by a mandrel surrounded by a bellows.
Figure 1:
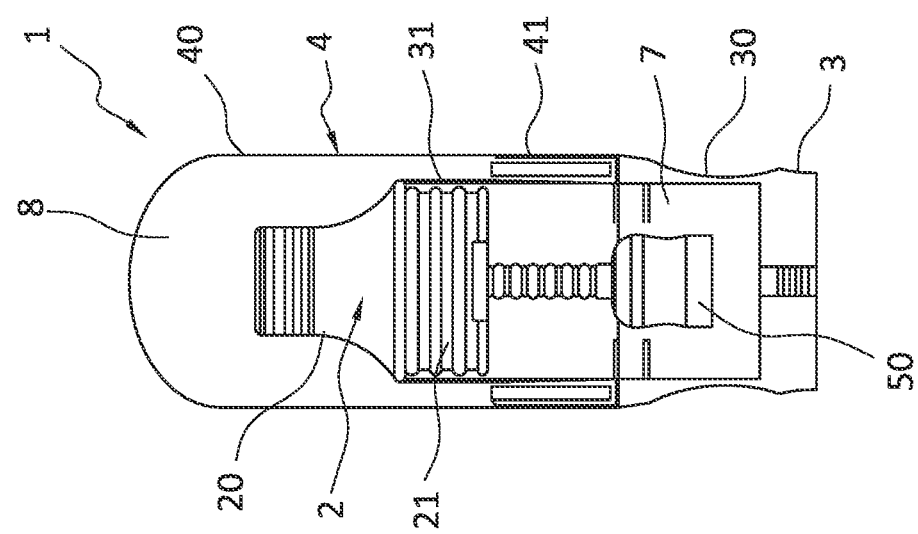
FIG. 1 is a view of a package of the invention in accordance with a first embodiment, inside which a medical component is packaged.
Figure 1C:
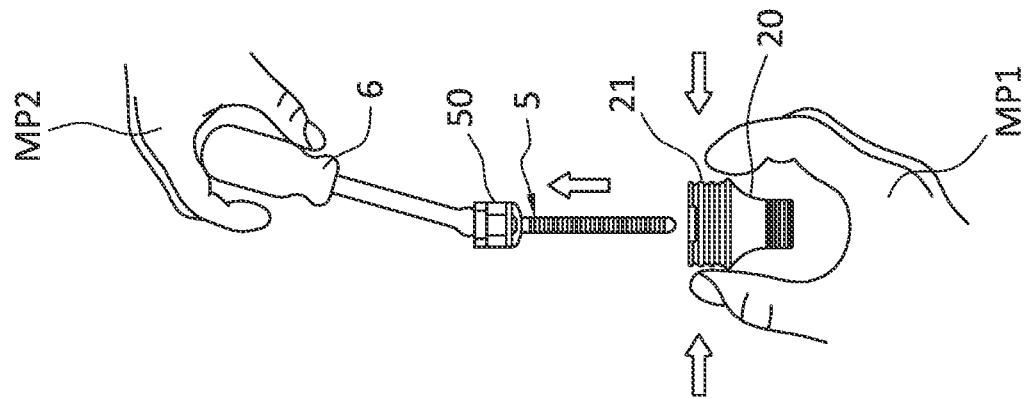
FIG. 1C is a view of the support element of the FIG. 1B package during a third step of unpackaging in which the third operator, who is holding the support element in one hand, uses the other hand to take hold of the medical component by means of a tool, so as to remove it from the support element, while deactivating the coupler means for coupling the medical component to the support element.
Figure 1B:
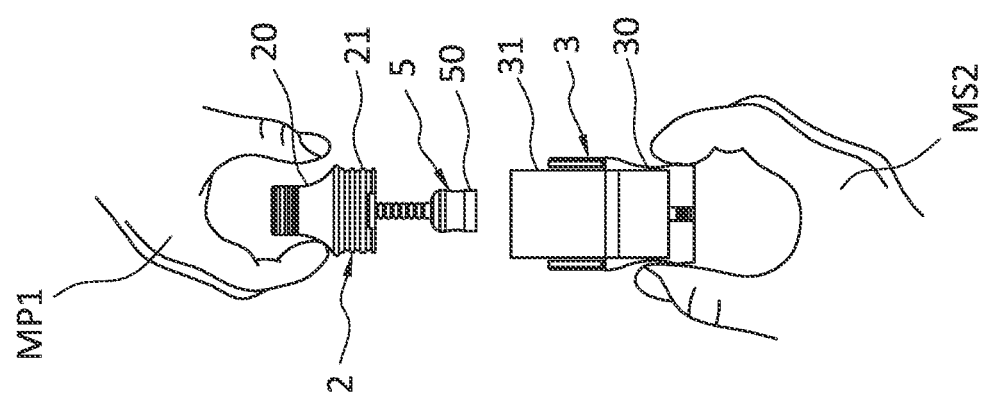
FIG. 1B is a view of the sub-assembly of the FIG. 1A package during a second step of unpackaging in which the stopper is removed, remaining in the hand of the second operator in the "dirty" zone, and the component support is held at its end remote from the medical component by the hand of a third operator in a clean zone.
Figure 1A:
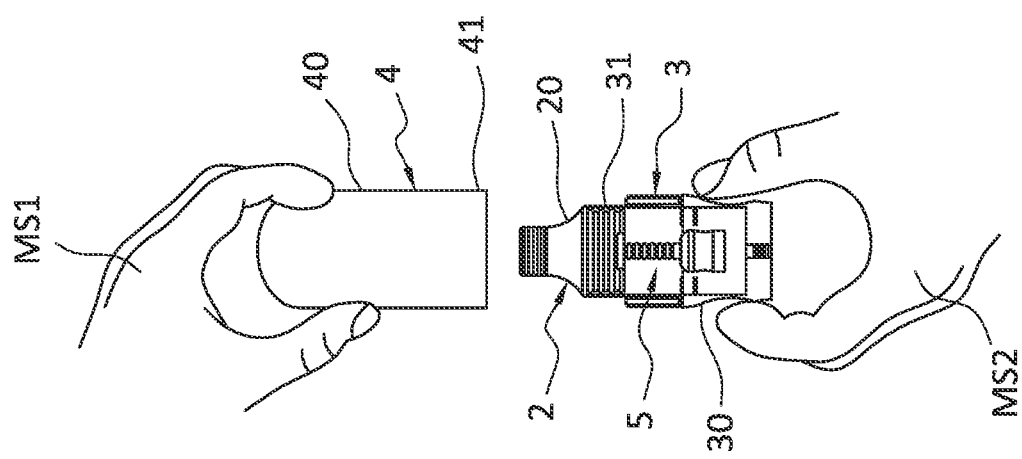
FIG. 1A is a view of the FIG. 1 package during a first step of unpackaging in which the cover is removed, remaining in the hand of a first operator in a "dirty" zone, and the remaining sub-assembly formed of the stopper and of the component support is held at its stopper end by the hand of a second operator in the "dirty" zone.

The term "dirty" or "contaminated" is used of a person working in non-acepticized conditions, who might contaminate, by hand, any object touched. Conversely, the term "clean" is used of a person working in conditions that are sufficiently aseptic.

With reference to the figures and as mentioned above, the invention provides a package 1 for an object, such as a medical component, for the purpose of preserving the sterile nature of the object, and in order to enable the object to be unpackaged in aseptic or near-aseptic conditions. In the embodiment shown in the figures, said object is a screw for surgery of the cervical spine or a screw for surgery of the lumbar spine, but the invention also applies to other types of object, in particular to other types of implant.

Said package includes a support element 2 provided with means 21; 22, 23; 24, 25; 26 for coupling said object 5 to said support element 2, and a first hollow protective element 3, referred to as a stopper, that can be coupled to the support element 2 of said object 5, by interfitting with partial overlap.

While the stopper 3 is coupled to the support element 2, said support element 2 and the stopper 3 define between them a first chamber 7 containing said object 5. Furthermore, the stopper 3 covers the support element 2 in part, such that the free end portion 20, referred to as the "grip end", of the support element 2 projects from said stopper 3 so that said free end portion 20 forms a grip zone.

When it is stated that the support element 2 is provided with means for coupling said object 5 to said support element 2, the term "coupling" means that said object cannot come apart from said support element without taking a specific action. Provision may be made for said object to be coupled to the support element by a narrow passage inside said first chamber, in such a manner as to prevent said object from escaping from said support element. Advantageously, provision may be made for said coupler means to also include breakable means making it possible to release the object from the support element.

Said package also includes a second hollow protective element 4, referred to as a cover, that can be coupled to the stopper 3 by interfitting with partial overlap, coming to cover the end 31 of said stopper 3, which itself covers the support element 2 of the object 5. The stopper 3 and the cover 4 are interfitted with partial overlap in such a manner as to define a second chamber 8 inside which the grip portion 20 of the support element 2 extends, and such that the end 30 of the stopper 3, remote from its end 31 of said stopper 3 that covers the support element 2, projects from the cover 4 such that said free end portion 30 of the stopper 3 forms a grip zone. The end 40 of the cover 4, remote from the stopper 3, also forms a grip portion of the package, remote from the end 30 of the stopper.

Thus, each element of the package, namely the support element 2, the stopper 3, and the cover 4, presents a grip end 20, 30, 40 remote from its opposite end that is interfitted with another element of the package. Said elements are interfitted in such a manner as to define a chamber 7, 8 between two interfitted elements, preferably a chamber that is sealed at least against bacteria. Thus, the interfitted elements of the package define two chambers 7, 8 of which one 7 is defined between the stopper and the cover, inside which the object is housed, and which can only be accessed once open, the other chamber 8 serving to protect the grip end 20 of the support element 2.

Such a design of the package makes it possible to handle it without any risk of contaminating the object contained in the presentation chamber and without having to let go of said object.

Specifically, the package held by the end 40 of the cover 4 by a first person in a dirty zone may be offered to a second person, also in a dirty zone, who takes hold of the opposite end 30 of the package formed by the free end of the stopper 3. The second person pulls on the stopper 3 in such a manner that the cover 4 remains in the hand of the first person, and this makes it possible to uncover a clean grip zone 20 of the support element 2, remote from the end 30 held by the second person. Specifically, the clean grip zone 20 of the support element 2 was previously housed in the chamber 7 defined between the cover 4 and the stopper 3. Then, said second person offers the remaining sub-package to a third person in a clean zone, who thus takes hold of the clean end 20 of the support element 2 that projects from the stopper 3. As above, the third person pulls on the support element 2 in such a manner as to keep hold only of said support element 2 and the object coupled to said support element. With the other hand, and by means of an appropriate instrument, the same operator removes the object from its support element 2 as described below. In a variant, the first person and the second person may be the same person.

Preferably, the stopper 3 and the cover 4 are each formed by a respective elongate hollow body that is open at one end and closed at the other end, i.e. a tube closed at one end. The design of each of the protective elements in the form of an elongate body like a test tube makes it possible to benefit from a safety distance between the grip end 40 of the cover 4 and the grip end 30 of the stopper 3.

Such a distance between the grip ends 30, 40 of the package makes it possible to limit the risk of contamination at the grip end 20 of the support element 2 that extends in the chamber 8, when said chamber 8 is opened by separating the cover 4 and the stopper 3. In addition, the distance between the grip end 30 of the stopper 3 and the grip end 20 of the support element 2 makes it possible to limit the risk of contamination while the support element 2 is being passed to a sterile "clean" operator, who can thus take hold of the support element by its free end 20 at a distance from the potentially-contaminated end 30 of the stopper.

In the embodiment shown in FIGS. 1, 1A, 1B, 1C, the means 21 for coupling the object to the support element comprise a deformable body 21, referred to as a valve, presenting an orifice, preferably of oval shape, that is capable of passing, by sideways deformation of said body relative to the axis of said orifice, from a "retaining" configuration in which said orifice of the valve 21 presents a shape and/or dimensions making it possible to clamp the object 5, to a "releasing" configuration in which said orifice presents a shape and/or dimensions making it possible to release said object 5 relative to said orifice of the valve 21.

In the relaxed state, the orifice of the valve 21 is naturally in the retaining position. Thus, for an orifice of shape that is oval or elliptical in its natural state, i.e. when relaxed, deforming said orifice by pressing sideways on the opposite ends of the ellipse or the oval, deforms the oval or elliptical orifice into a substantially-circular orifice of diameter that is greater than the minor diameter of the ellipse or oval, and this makes it possible to release the object that is no longer pressed against the wall of the orifice. Naturally, the orifice of the valve is dimensioned so that in its non-deformed state, its minor diameter is less than the diameter of the object, but in its deformed state, its minor diameter is greater than said diameter of the object.

In another embodiment of the coupler means shown in FIG. 2, that finds an advantageous application for an object presenting an elongate body, said means 22, 23 for coupling the object to the support element include a deformable elongate body 22, referred to as a mandrel, along and inside which an orifice is formed for inserting the object.

Said means 22, 23 also include a bellows 23 that is threaded on the mandrel 22 and that is capable of passing from a deployed position of the folds of the bellows, in which said bellows bears against the mandrel 22 in such a manner as to clamp the insertion orifice around the object 5, to a compressed position of said folds of the bellows, in which the bellows does not press against the mandrel 22 so that the orifice is unclamped and the object is free to move relative to the orifice.

When the mandrel is relaxed, the orifice of the mandrel 22 is dimensioned to present an opening that is large enough to receive the elongate body of the object, without damaging or rubbing against the mandrel.

In the deployed configuration of the bellows along the mandrel, i.e. in the free configuration of the folds of the bellows, said bellows bears via its top portion against the top portion of the mandrel, such that the inner wall of the orifice of the mandrel clamps on the body of the object, at the opening for inserting the body in the mandrel.

In order to couple the object to the assembly formed of the mandrel and of the bellows, the bellows is compressed so as to relax the orifice of the mandrel in order to make it possible to insert the body of the object into said orifice, then the bellows is released so that it bears against the mandrel in such a manner as to clamp the orifice around the body of said mandrel. The object is released by compressing the bellows so that the orifice is no longer pressed around the object, and so as to make it possible to remove it by means of an instrument.

Preferably, as shown in FIG. 2, said support element 2 also includes at least two arms 27 that are spaced apart from each other and that extend on either side and along the assembly formed of the mandrel 22 and of the bellows 23.

Said arms project from the support-element portion that is provided with coupler means for coupling the object and they extend along the axis for interfitting said support element with the stopper, in such a manner as to co-operate with the wall of the stopper for interfitting the stopper and the support element, with partial overlap.

In particular, the stopper 3 covers the arms 27 in such a manner that the arms make it possible to guide and stiffen the stopper and support-element assembly while protecting the bellows 23 relative to the stopper 3 so that said bellows are not deformed while the stopper is being closed or opened relative to the support element.

The space between the arms enables the operator to access the bellows so as to compress it in order to insert or release the object held in the orifice of the mandrel.

Figure 4:
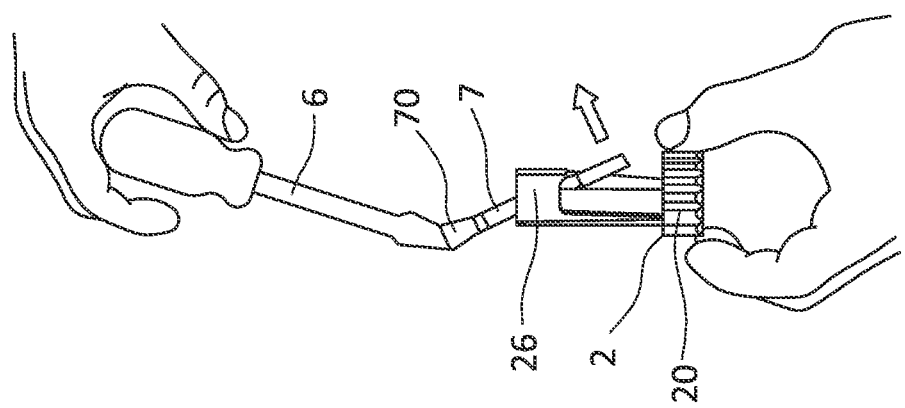
FIG. 4 is a section view of the support element in a fourth embodiment of the package in which the coupler means for coupling the medical component to the support element are formed by an element presenting a housing that is suitable for holding the component in a given orientation and for enabling it to be released by turning or tilting, thereby disengaging said component sideways.

In another embodiment of the invention shown in FIG. 4, the means 26 for coupling the object to the support element present a configuration for holding the object captive in a given orientation of said object, and a configuration for releasing said object by pivoting it. Provision may be made for the coupler means 26 to include a housing in which the object is held by resilient clamping or by snap-fastening. In the embodiment shown in FIG. 4, the object is a cervical screw 7 having a head 70 that is suitable for co-operating with the instrument 6 so as to enable the operator to pivot the body of the screw 7 in order to release it from the coupler means 26. In particular, the object is released by pivoting it about an axis that is orthogonal to the axis of the housing and that corresponds to the longitudinal axis of the object.

Figure 3:
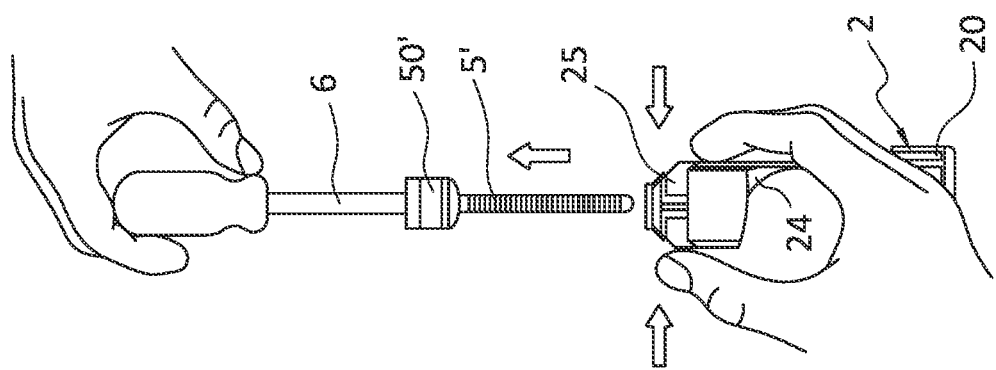
FIG. 3 is a section view of the support element in a third embodiment of the package in which the coupler means for coupling the medical component to the support element are formed by a valve-type deformable element having an orifice that is configured so as to clamp onto the medical component that passes therethrough, thereby coupling it to the support element, and so as to release said component when said valve is deformed.
Figure 8:
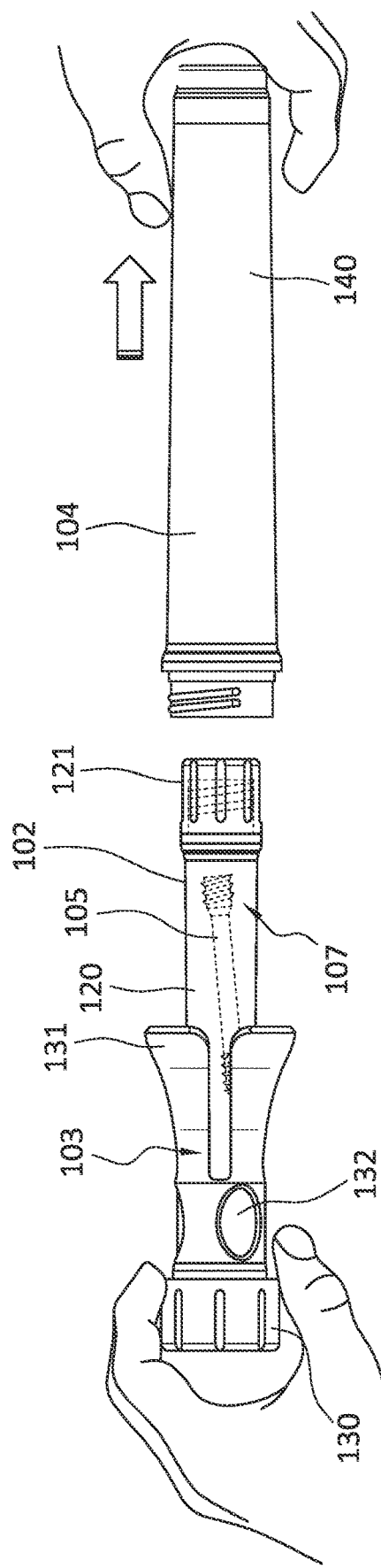
Figure 9:
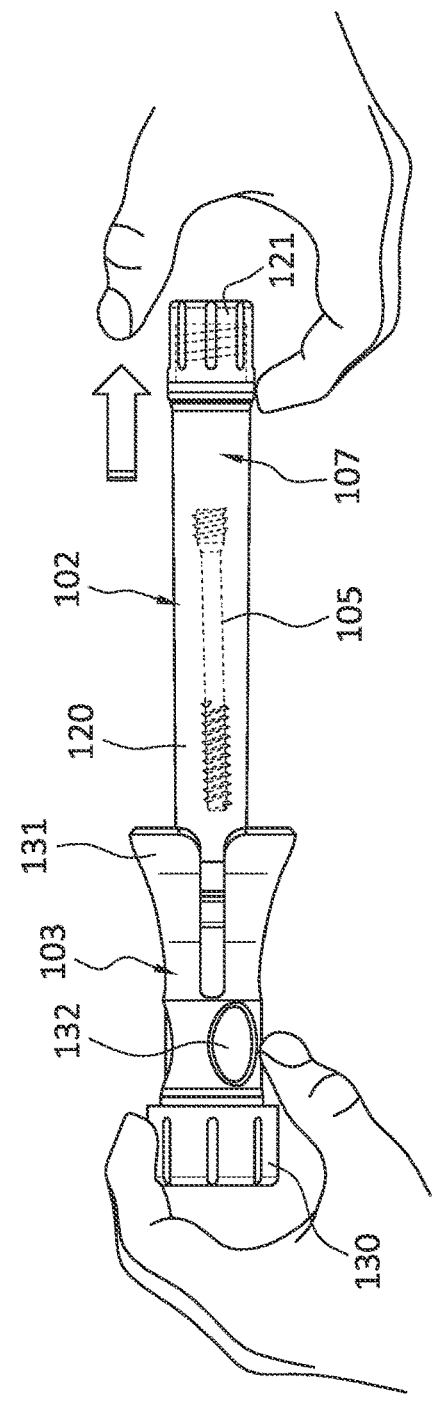
FIGS. 9 and 10 are views of the sub-assembly of the package from FIG. 8 during a second unpacking step in which the stopper is withdrawn, remaining in the hand of the contaminated person, and the support element of the article is held by the hand of a second person called the clean person.
Figure 10:
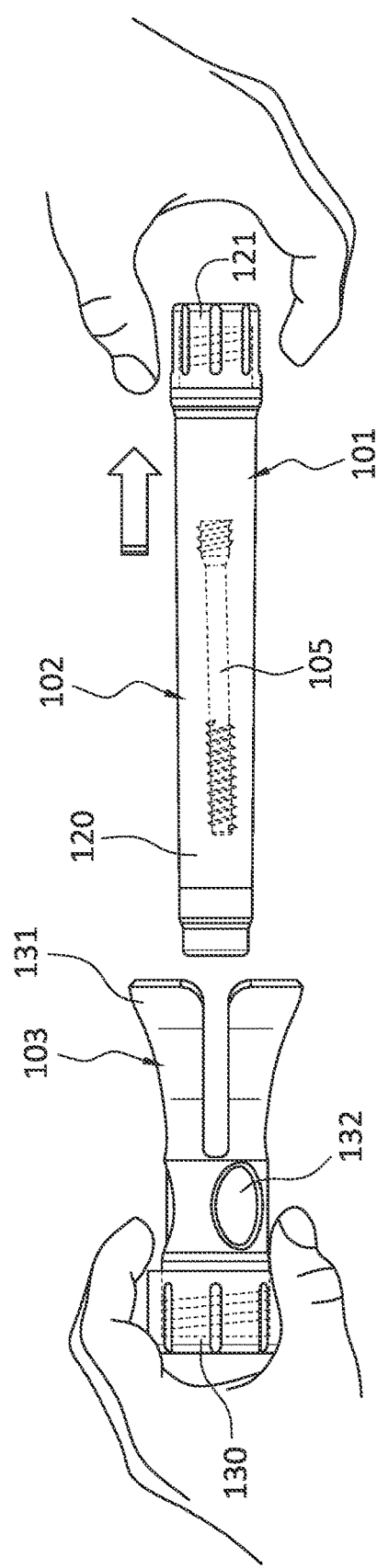
Figure 11:
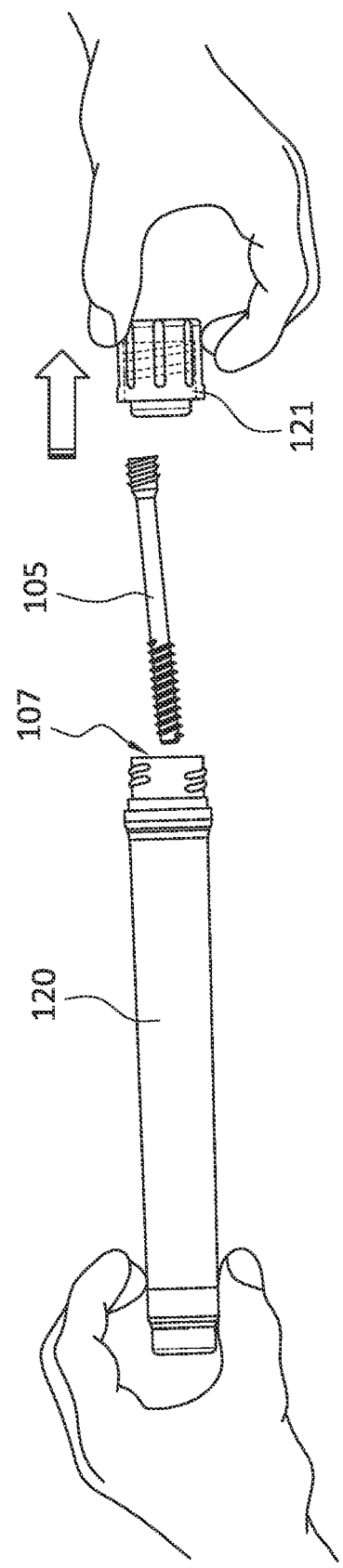
FIG. 11 is a view of the support element from FIG. 9 during a third unpacking step in which the clean person separates the two components forming the support element in order to remove the medical component therefrom.

In particular embodiments of the invention shown in FIGS. 3 and 4, the support element 2 and the means 24, 25; 26 for coupling the object to the support element are configured to hold the object suspended through said coupler means, in such a manner as to make it possible to see the length of said object while said object is coupled to the support element 2.

To this end, the support element comprises a generally stem-shaped portion having a top portion that is fitted with coupler means, and this makes it possible, for a screw-type object, to suspend said screw by its body at a height close to the screw head so that the screw is held in reliable manner on the support element, while enabling the operator to see the length of the screw body.

Specifically, in the embodiment shown in FIG. 3, the valve 25 is positioned at the top portion of the stem so that the object that passes through the valve may extend into the space left free between the valve and the bottom portion of the stem. Thus, the length of the object remains visible and the object may be held correctly.

For an object formed of a plurality of hinged-together portions, holding the object suspended also makes it possible to hold said object at said hinge so as to secure it. This is the situation shown in FIG. 3 for which the object suspended through the valve is a "tulip" screw 5' having a head 50' that is hinged to the body via a ball joint. Said screw may be engaged in the orifice of the valve until its head comes into abutment against the edge of the orifice, and this makes it possible to wedge the screw securely, without any risk of the body of the screw moving relative to its head.

In the embodiment shown in the figures, said elements 2, 3, 4 of the package are interfitted, with partial overlap, merely by friction, e.g. by elastic clamping or pressure. Such interfitting, with partial overlap, merely by friction makes it possible to separate said elements by one or both of the operators pulling on one element of the package in natural manner. It is also possible to envisage interfitting, with partial overlap, by clipping.

In a variant, interfitting, with partial overlap, could be achieved by screw-fastening. For screw-fastening, the thread and the tapping formed on the elements to be interfitted are configured in such a manner as to enable said elements to be screw-fastened together only once. In particular, provision may be made for the thread and/or the tapping to deform while screwing on and off, so that the two elements cannot be screwed back together again.

Preferably, the chambers 7 and 8 are impermeable, at least to bacteria. Provision may also be made for them to be impermeable to any fluid. In a variant, provision may be made for one and/or the other of the chambers, and preferably at least the presentation chamber 7 for presenting the object, to be permeable only to gas so as to enable the chamber(s) to be sterilized with gas.

Thus, in a particular embodiment of the invention, provision may be made for at least a portion of the wall of the stopper 3 that defines a portion of the presentation chamber 7 for presenting the object 5 to be formed of material that is permeable to gas but impermeable to bacteria, so as to enable the presentation chamber and the object, e.g. a medical component to be sterilized with gas, e.g. with ethylene oxide or steam. Such a design of the package makes it possible to sterilize the chamber(s) other than by using radiation.

Provision may thus be made for the stopper to be closed, at its end remote from the end that covers the support element in part, by a membrane that is adapted to sterilization by means of a gas.

Advantageously, said object 5 is coupled to the support element 2 in such a manner that its grip end 50 is free and points away from the grip portion 20 of the support element 2 so that the grip zone faces the instrument for gripping the object, and this makes it possible to grip the object easily and rapidly.

The support element 2 and/or the stopper 3 and/or the cover 4 present(s) a portion, preferably formed by a membrane, that is impermeable to bacteria but permeable to gas so as to enable said first chamber 7 and/or said second chamber 8 to be sterilized with gas.

The method of unpackaging an object contained in a package as described above is described below by means of FIGS. 1A, 1B, and 1C in the context of passing a medical component to a "clean" operator, specifically the surgeon in the operating block, via two other operators who are "dirty", i.e. working in a potentially-contaminated environment.

The first operator takes hold of the complete package containing the medical component 5 via the free end 40 of the cover 4 by means of a "dirty" hand MS1. Said first operator thus offers the package to the second operator who takes hold of it via the free end 30 of the stopper by means of a hand MS2 that is also "dirty". With each of the operators holding a respective end of the package in a respective hand, at least one of the two pulls on the package so that the cover is separated from the stopper, while the stopper to which the support element of the medical component is coupled remains in the hand MS2 of the second operator. The distance between the ends 30 and 40 of the package makes it possible to reduce the risk of the support element being contaminated when the chamber 8 is opened by separating the cover and the stopper. As mentioned above, the first operator and the second operator may be the same person.

The grip portion of the support element uncovered in this way remains clean and may be presented to the third operator, namely the surgeon, who uses a "clean" hand MP1 to take hold of said clean end of the support element that is remote from the end 30 of the stopper held by the hand MS2 of the second operator.

At least one of the second and third operators pulls on the sub-assembly formed of the support element and of the stopper so that the presentation chamber 7 for presenting the object opens by means of said support element 2 held by the hand MP1 of the third operator separating from the stopper 3 that remains in the hand MS2 of the second operator.

The third operator can then use the hand MP1 that is holding said support element to deactivate the coupler means without letting go of said support element, and can use the other hand MP2, a "clean hand, to take hold of the object via its free end 50 by means of an instrument 6 in order to implant said object in the body of the patient.

In the embodiment shown in the figures, the support element defines an open cavity housing the object 5, which cavity is to be closed by the stopper 3.

In a variant embodiment that is not shown in the figures, said support element alone defines said first chamber containing said object. To this end, said support element is formed of at least two parts that can be coupled and uncoupled relative to each other, preferably by interfitting with partial overlap, so as to form said first chamber containing said object. In other words, one of the parts of said support element is for closing the open cavity formed by the other part.

In this variant, said stopper is formed by a hollow body having a base portion that includes coupler means for coupling to the support element. Advantageously, the coupler means are configured in such a manner as to make it possible to couple the object to the part of the support element that forms the grip portion of said support element, i.e. the part of the support element that is not directly coupled to the stopper. The stopper and the support element are interfitted by force-fitting an end portion of the support element in a corresponding hollow portion of the stopper. To this end, the hollow portion of the stopper presents lugs that are to be flattened by the support element while said support element is being force-fitted in the stopper. Said lugs are distributed over the inner peripheral face of said stopper around the axis of the stopper.

In such a variant embodiment of the support element, the method described above may be adapted as follows. After the support element 2, held by a clean person, has been separated from the stopper 3, held by a person who might be contaminated, provision may be made for the support element 2 that closes the object 5 to be put in a standby zone, while said object 5 is waiting to be used. Then, said clean person, or another clean person, may open the first chamber 7 defined by said support element 2 by separating the two parts that form said support element, e.g. by unscrewing them, in order to take hold of said medical component.

Thus, the medical component has been neither touched nor let go of during its unpackaging. Furthermore, the chamber containing the medical component is opened only in a clean zone.

As a result of the cover that defines a protective chamber for protecting the grip portion 20 of the support element 2, the clean person touches a clean portion of the package. Specifically, the dirty portions of the package, namely the stopper 3 and the cover 4, remain in the hands of the dirty person. Thus, the hand of the person who takes hold of the support element remains clean.

Preferably, the chambers 7 and 8 are impermeable, at least to bacteria. Provision may also be made for them to be impermeable to any fluid. In a variant, provision may be made for one and/or the other of the chambers, and preferably at least the presentation chamber 7 for presenting the object, to be permeable only to gas so as to enable the chamber(s) to be sterilized with gas.

Thus, in a particular embodiment of the invention, provision may be made for at least a portion of the wall of the stopper 3 that defines a portion of the presentation chamber 7 for presenting the object 5 to be formed of material that is permeable to gas but impermeable to bacteria, so as to enable the presentation chamber and the object, e.g. a medical component to be sterilized with gas, e.g. with ethylene oxide or steam. Such a design of the package makes it possible to sterilize the chamber(s) other than by using radiation.

In particular, provision may thus be made for the stopper to be closed, at its end remote from the end that covers the support element in part, by a membrane that is adapted to sterilization by means of gas.

With reference to the figures, and as has been mentioned above, further embodiments of the invention relates to a medical assembly comprising a medical article 105 and a package 101 containing said article 105 for the purpose of preserving the sterile nature of the article and with a view to unpacking said article in aseptic or almost aseptic conditions. Said article can be, for example, a solid component, such as a surgical screw, or any other type of article, in particular any other type of implant. In addition, said article can be a liquid or a powder. Said article and, preferably, the various parts of the package are sterilized as detailed below.

Said package comprises a hollow support element 102 inside which said article 105 is free. In other words, said article 105 can move freely inside the support element 102. Said package also comprises a first protective element 103, called a stopper, which can be coupled to the support element 102 of said article 105 by engagement with partial overlap, in such a way that the support element 102 has a grip part 120 that protrudes from said stopper 103. Said grip part 120 corresponds to the free end part of the support element 102 which protrudes from said stopper 103. As is explained in detail below, said support element 102 delimits on its own, or in cooperation with the stopper 103, a first chamber 107 that encloses said article 105.

Said package also comprises a second hollow protective element 104, called a cover. Said cover 104 is able to be coupled to the stopper 103, by engagement with partial overlap, in such a way as to delimit, in cooperation with said stopper 103, a second chamber 108 inside which there extends the grip end 120 of the support element 102. In the state when the cover 104 is coupled to the stopper 103, a part 130 of the stopper 103 protrudes from the cover 104.

Said part 130 of the stopper corresponds to the free end of the stopper 103, opposite the end 131 of said stopper 103 that covers part of the support element 102 and forms a grip area. The end 140 of the cover 104 opposite the stopper 103 also forms a part for gripping the package opposite the end 130 of the stopper.

Thus, each element of the package, namely the support element 102, the stopper 103 and the cover 104, has a grip end 120, 130, 140 in relation to its opposite end coupled to another element of the package. Said elements engage with each other in such a way as to define, by cooperation of two engaged elements, a chamber 107, 108 which is preferably impervious at least to bacteria. Thus, the engaged elements of the package define two chambers 107, 108, of which one 107 is defined between the stopper and the cover, accommodates the article and can be accessed only when opened, the other chamber 108 serving to protect the grip end 120 of the support element 102.

Such a design of the package allows it to be manipulated without risk of contamination of the article contained in the presentation chamber, without having to let go of said article contained in the support element, while at the same time allowing said article to be quickly taken hold of, since the article is free in the support element.

In the example illustrated in the figures, said support element 102 on its own delimits said first chamber 107 enclosing said article 105. For this purpose, said support element 102 is formed by at least two components 120, 121 that can be coupled to/uncoupled from each other, by engagement with partial overlap, in order to form said first chamber enclosing said article 105.

An embodiment can also be provided according to which said support element 102 on its own delimits said first chamber 107 by being formed in one piece. Said support element 102 can thus be in the form of a closed and divisible one-piece hollow body, such as a divisible ampule, containing said article. In this case, the chamber 107 is opened by breaking said ampule.

According to a variant that is not illustrated, said support element delimits, in cooperation with the stopper, said first chamber that encloses said article. In this case, said support element delimits an open cavity intended to be closed by said stopper.

Preferably, the stopper 103 is formed by an elongate hollow body that is open at one end and closed at the other end. In the example illustrated in the figures, the cover 104 is also formed by an elongate hollow body that is open at one end and closed at the other end. The support element 102 is also in the form of an elongate hollow body that is closed at one end and open at the other end, or closed at both ends and formed by at least two components, depending on the embodiment chosen.

The design of the stopper 103 and of the cover 104 in the form of an elongate body, in the manner of a test tube or of a tube closed at least at one end, provides the benefit of, on the one hand, a safe distance between the grip end 140 of the cover 104 and the grip end 130 of the stopper 103, and, on the other hand, a safe distance between the grip end 120 of the support element 102 and the grip end 130 of the stopper 103.

Such a distance between the grip ends 130, 140 of the package makes it possible to limit the risk of contamination in the area of the grip end 120 of the support element 102 that extends in the chamber 108, when said chamber 108 is opened by separation of the cover 104 and the stopper 103.

Said stopper 103, and if appropriate the cover 104, has (have) at least two predefined locations 132 that each permit the positioning of at least one finger of a person in order to allow him to grip said stopper or said cover by gripping between at least two fingers. Preferably, at least two of said predefined locations 132 are diametrically opposite with respect to the axis of the element, i.e. stopper 103 or cover 104, on which they are formed. In the example illustrated in FIGS. 5 to 12C, each location 132 is formed on a portion of the stopper that is intended to be covered by the cover 104. In this case, said location becomes accessible once the cover has been withdrawn.

Figure 12B:
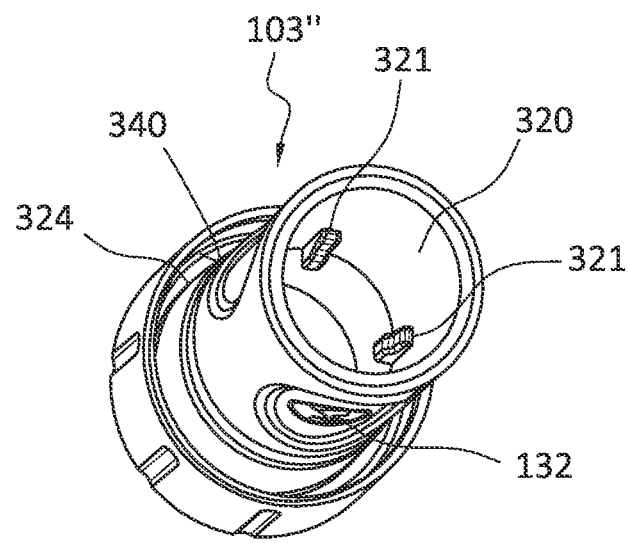
FIG. 12B is a perspective view of another variant of the stopper of the package according to the invention, with an area for positioning of the fingers which is called an internal area and is formed on that part of the stopper intended to extend inside the cover.
Figure 12A:
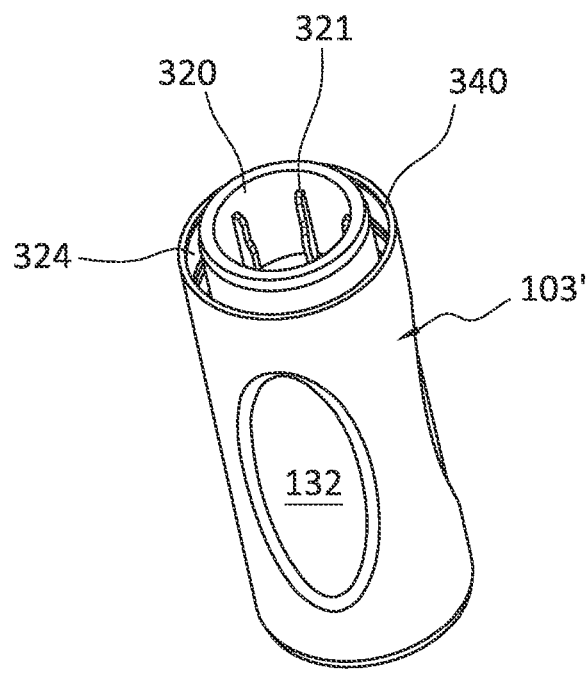
FIG. 12A is a perspective view of a variant of the stopper of the package according to the invention, with an area for positioning of the fingers which is called an external area and is formed on that part of the stopper intended to protrude from the cover.
Figure 12C:
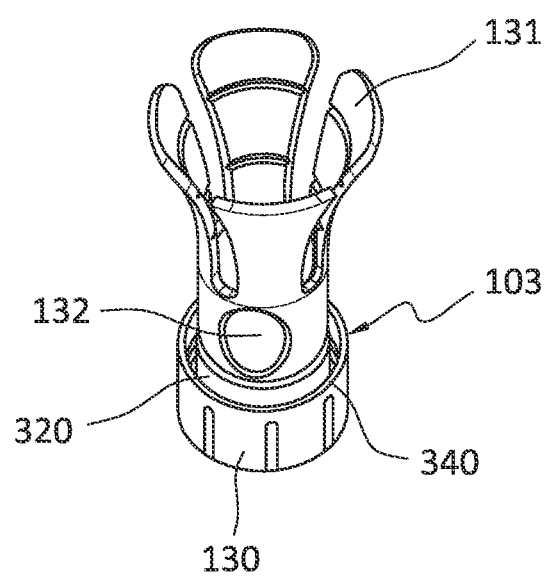
FIG. 12C is a perspective view of the stopper of the package according to the first embodiment of the invention.

According to another embodiment of the stopper 103' illustrated in FIG. 12A, said location 132 is formed on a portion of the stopper 103' that is not intended to be covered by the cover.

Advantageously, the stopper 103; 103' has a sufficient length to allow the person to position his fingers on said stopper, and in particular to grip the stopper with a thumb, without risk of touching the support element 102.

Said support element 102 and protective elements 103, 104 of the package engage each other, with partial overlap, by friction and/or by screwing. The means for coupling the elements to each other are explained in detail below.

In the example illustrated in the figures, the stopper 103 and the cover 104 engage with each other by screwing, as do the parts 120, 121 of which the support element 102 is composed. Preferably, the thread and the tapping formed on the elements which engage with each other are configured in such a way as to allow said elements to be screwed together only once. In particular, provision can be made that the thread and/or the tapping deform during the screwing and unscrewing, such that renewed screwing of the two elements with each other is no longer possible.

Alternatively, the partially overlapping engagement of said elements of the package could be achieved by simple friction, for example by elastic clamping or pressure. Such engagement by simple friction makes it possible to disengage said elements by means of one or each of the persons simply pulling an element of the package in a natural movement. Engagement by clips is also conceivable.

In the example illustrated in FIGS. 5 to 12C, said stopper 103 also has at least one deformable part 131, preferably at least one deformable wing, allowing said stopper to be partially engaged inside the cover. Said part 131 is configured such that, on the one hand, when said deformable part 131 of the stopper is covered by the cover, said part 131 comes to bear against the internal face of the cover 104 in order to allow the stopper to be coupled to the cover by friction, and, on the other hand, such that said part 131 is able to deform in order to permit the separation of the cover 104 from the stopper 103.

Said stopper 103 is formed by a hollow body open at one end and closed at the other end. The cover 104 is also formed by a hollow body open at one end and closed at the other end. The closed end of the stopper 103 defines a bottom part of the stopper. As is explained in detail below, said stopper 103 comprises means for coupling to the support element 102.

In particular, said stopper 103 comprises a body substantially of revolution about an axis corresponding to the longitudinal axis of said stopper 103. The body of the stopper comprises a peripheral wall 320 called an internal wall, and a peripheral wall 340 called an external wall which surrounds said internal peripheral wall 320.

The external peripheral wall 340 is substantially coaxial to the internal peripheral wall 320.

Said external peripheral wall 340 surrounds said internal peripheral wall 320 with clearance in order to define, between said peripheral walls, an annular space 324 for insertion of that part of the cover 104 intended to be coupled to said stopper 103. Said part of the cover 104 intended to be coupled to said stopper 103 corresponds to the open end of the cover 104.

On the external 340 and/or internal 320 peripheral walls, provision can be made to form screwing means, such as a tapping and/or thread, able to cooperate with complementary screwing means, such as a thread and/or tapping, formed on the peripheral wall of the cover 104.

In particular, the internal face of the peripheral wall 340 called the external wall and/or the external face of the peripheral wall 320 called the internal wall can have a tapping and/or a thread in order to cooperate with a complementary thread and/or tapping formed on the external peripheral face and/or the internal peripheral face of the body of the cover 104.

In the example illustrated in the figures, the internal face of the external peripheral wall 340 has a tapping able to cooperate with a thread formed on the external face of the peripheral wall of the cover 104.

Provision can also be made that the distance between the external 340 and internal 320 peripheral walls of the stopper is configured such that the engagement of the cover 104 with the stopper 103 causes the peripheral wall of the cover 104 to be pinched between the external 340 and internal 320 peripheral walls of the stopper.

In the example illustrated in the figures, the stopper 103 and the support element 102 engage with each other by force, that is to say by pressing an end part of the support element 102 into a corresponding hollow part of the stopper 103.

In other words, the internal face of the internal peripheral wall 320 of the stopper 103 has retaining means 321 for retaining the part of the support element 102 engaged by force inside the space delimited by the internal peripheral wall 320 of the stopper 103.

Advantageously, said retaining means 321 comprise lugs which are intended to be in bearing contact with the support element 102 in the state when said support element 102 is driven into the stopper 103. A good retention of the support element 102 with the stopper 103 is thus obtained before their separation with a view to opening said first chamber 107. In particular, each lug has a ramp-forming part configured such that the support element 102, which is engaged in the internal peripheral wall 320, pushes the lugs radially outward and thus deforms the corresponding internal peripheral wall 320 toward the external peripheral wall 340.

More precisely, as is illustrated more particularly in FIGS. 12A and 12B, the lugs 321 are distributed on the internal peripheral face of the stopper, about the axis of said stopper 103, preferably being spaced apart at angles from one another.

The presence of said lugs inside the internal peripheral wall 320 of the stopper makes it possible to retain the support element 102 engaged by force in the stopper 103, while also ensuring that, on such engagement of the support element 102 in the internal peripheral wall of the stopper, the internal peripheral wall 320 of the stopper is brought closer to the external peripheral wall 340 of said stopper, this being caused by the support element 102 bearing on the lugs 321.

The closing together of the internal 320 and external 340 peripheral walls by elastic deformation reinforces the leak tightness of the join in the area of engagement between the cover 104 and the stopper 103. This is because the peripheral walls 320, 340 can thus pinch the peripheral wall of that part of the stopper 103 engaged in the space formed between said internal 320 and external 340 peripheral walls of the stopper.

Thus, said retaining means 321 formed inside the internal peripheral wall 320 of the stopper 103 make it possible to improve not only the hold of the support element 102 with respect to the stopper 103, but also the leak tightness between the stopper 103 and the cover 104, of which the peripheral wall is pinched between said internal 320 and external 340 peripheral walls of the stopper 103.

In the example illustrated in the figures, the hold between the cover 104 and the stopper 103 is ensured by the complementary screwing means, of the thread and tapping kind, formed on the cover 104 and the stopper 103, and the leak tightness between the cover 104 and the stopper 103 is obtained by pinching the peripheral wall of the cover 104 between said peripheral walls 320 and 340 of the stopper 103, resulting from the engagement of the support element 102 in the stopper 103 which elastically deforms the peripheral wall 320 toward the peripheral wall 340 of the stopper 103. The retention of the support element 102 in the stopper 103 is ensured by the lugs 321 which enclose the support element 102.

In addition, the lugs 321 form spacers between the peripheral wall 320 and the support element 102, which spacers allow a radial distance to be maintained between the support element 102 and the peripheral wall 320. In addition, the spacing between the lugs 321 makes it possible to define a space for fluid communication between the inside of the peripheral wall 320 and the inside of the cover 104.

A communication passage of this kind between the inside of the cover 104 and the inside of the peripheral wall 320 ensures that a sterilization gas injected into the cover 104, for example via a membrane permeable to gas and preferably impermeable to bacteria, is able to spread inside the volume delimited by the peripheral wall 320, in order to sterilize the two chambers 107 and 108 of the package, especially when the support element 102 is an open element, or when that end of the support element 102 engaged in the peripheral wall 320 has a membrane permeable to gas and preferably impermeable to bacteria.

Provision can be made that the retaining means 321 for retaining the support element 102 with respect to the stopper 103 also comprise screwing means, for example of the tapping kind, which are able to cooperate with complementary screwing means, for example of the thread kind, which are formed on the external face of the peripheral wall of the support element 102.

The combination of screwing means and of lugs thus makes it possible to combine a retention of the support element 102 with respect to the stopper 103 by screwing and also by friction, while maintaining the aforementioned advantages of the join between the stopper 103 and the cover 104.

In addition, in the example illustrated in the figures, the internal peripheral wall 320 protrudes from the external peripheral wall 340 at the end opposite the bottom of the stopper 103.

According to the stopper variants that are illustrated in FIGS. 12A and 12B, the stoppers 103'; 103" also each have a hollow part which is provided with lugs and into which an end part of the corresponding support element is intended to be driven.

The support element 102 and/or the stopper 103 and/or the cover 104 have a part, preferably formed by a membrane, that is impermeable to bacteria but permeable to gases in order to permit gas sterilization of said first chamber 107 and/or of said second chamber 108.

With the package described above, it is possible to carry out a method of unpacking that comprises the following steps. This method is described with reference to FIGS. 5 to 12 in which the support element is composed of two components which can be coupled/uncoupled in order to delimit a closed cavity that encloses said article. As is illustrated in FIGS. 5 to 9, a first person, presumed to be in a contaminated area, separates the cover 104 from the stopper 103 in such a way as to uncover the support element 102, which remains away from the hands of the person who is presumed to be contaminated, since the hand of said person holds the remaining package by the stopper 103, that is to say at a distance away from the support element. The contaminated person can then offer to a second person, presumed to be in a clean area, the remaining package via the support element 102. Said clean person can then pull the support element 102 in order to cause the separation of said support element 102 from the stopper 103 held by the first person, who is presumed to be contaminated. Said "clean" person is, for example, the surgeon in the operating theater.

If appropriate, the support element 102 which encloses the article 105 can be kept in a stand-by area pending the use of said article 105. Then said second person, or another person presumed to be clean, can open the first chamber 107 defined by said support element 102 by separating, in this case by unscrewing, the two components 120, 121 which form said support element, in order to take hold of said medical component.

In the case not illustrated in the figures, where the support element directly forms the first chamber accommodating said article in cooperation with the stopper, the method described above is adapted such that the contaminated person offers to the second person, presumed to be in a clean area, the remaining package via the support element 102, by orienting said remaining package in such a way that the support element 102 is at a height lower than that of the stopper 103, such that said article 105 remains contained in the support element 102 during the separation of said support element 102 from the stopper 103, so as to avoid said article 105 falling to the ground.

Thus, the medical component has not been touched or let go of during its unpacking. In addition, the chamber containing the medical component is opened only in a clean area.

By virtue of the cover which delimits a chamber protecting the grip part 120 of the support element 102, the clean person touches a clean part of the package. This is because the dirty parts of the package, namely the stopper 103 and the cover 104, have remained in the hands of the dirty person. It is thus ensured that the hand of the person taking hold of the support element remains clean.

Of course, in each of the embodiments, provision can be made that the separation of the cover and the stopper is carried out by two different persons in a contaminated area instead of by only one person, one of them holding an end of the stopper and the other holding an end of the cover.

Preferably, the chambers 107 and 108 are impermeable at least to bacteria. Provision can be made that they are also impermeable to any fluid. Alternatively, provision can be made that one or other of them, preferably at least the chamber 107 for presentation of the article, is permeable only to gases in order to permit gas sterilization of the one or more chambers.

Thus, according to a particular embodiment of the invention, provision can be made that at least part of the wall of the stopper 103 delimiting part of the chamber, or 107 for presentation of the article 105 is made of material permeable to gas but impermeable to bacteria, in order to permit gas sterilization of the chamber for presentation of the article, for example a medical component, for example with ethylene oxide or by steam. Such a design of the package allows the one or more chambers to be sterilized other than by radiation.

Provision can thus be made that the stopper, at its end opposite the one partially covering the support element, is closed by a membrane designed for gas sterilization.

The present invention is not in any way limited to the embodiments that have been described and illustrated, and instead a person skilled in the art will be able to apply any variant thereof that he sees fit.

What is claimed is:

1. A medical package containing a medical article, comprising:
    a support element comprising a hollow support tube, wherein the support element includes a first chamber configured to enclose the medical article and wherein the support element includes a support structure configured to hold the medical article captive;
    a stopper configured to be coupled to the support element, wherein the support element has a grip part that protrudes from the stopper, the grip part of the support element configured to be held by a hand of a person;
    a hollow protective cover configured to be coupled to the stopper in such a way as to delimit, in cooperation with the stopper, a second chamber inside which there extends the grip part of the support element, wherein the hollow protective cover configured to be separated from the stopper,
    wherein when the hollow protective cover is coupled to the stopper, a part of the stopper protrudes from the hollow protective cover, and is configured to form a grip end of the stopper that is configured to be held by a hand of a person, when the hollow protective cover is separated from the stopper, and
    wherein a part of the support element is configured to be engaged by force inside the stopper, and when the hollow protective cover is separated from the stopper, the support element remains coupled to the stopper while the support element is also separable from the stopper when a person holds the grip part of the support element and pulls the support element so as to separate it from the stopper.

2. The medical package of claim 1, wherein the stopper comprises an internal peripheral wall, and an external wall peripheral wall which surrounds the internal peripheral wall with clearance in order to define, between the peripheral internal and external walls, an annular space for engagement of that part of the hollow protective cover configured to be coupled to the stopper, the internal peripheral wall defining a space for engagement of that part of the support element configured to be coupled to the stopper.

3. The medical package of claim 2, wherein an internal face of the internal peripheral wall of the stopper is provided with retaining means for retaining that part of the support element engaged inside the space delimited by the internal peripheral wall of the stopper.

4. The medical package of claim 3, wherein the retaining means comprise lugs which are configured to be in bearing contact with the support element in the state when the support element is engaged in the stopper, and wherein the lugs are distributed on the internal peripheral face of the stopper, about the axis of the stopper, by being spaced apart at angles from one another.

5. The medical package of claim 4, wherein each lug comprises a ramp-forming part, directed toward the axis of the stopper starting from a bottom point of the ramp situated at the open end of the stopper to a top point of the ramp situated at the closed end of the stopper, in such a way that, when the support element is engaged inside the space defined by the internal peripheral wall of the stopper, the support element, by bearing on the ramp, pushes the lug radially and deforms the corresponding internal peripheral wall toward the external peripheral wall.

6. The medical package of claim 4, wherein the lugs form spacers for maintaining a radial distance between the support element and the internal peripheral wall of the stopper, the spacing between the lugs defining a space for fluid communication between the inside of the internal peripheral wall of the stopper and the inside of the hollow protective cover.

7. The medical package of claim 2, wherein at least one of the external and internal peripheral walls of the stopper comprise screwing means for cooperating with complementary screwing means formed on the hollow protective cover.

8. The medical package of claim 7, wherein the internal face of the external peripheral wall of the stopper has a tapping that is able to cooperate with a thread formed on the external face of a peripheral wall of the hollow protective cover.

9. The medical package of claim 1, wherein, the support tube and support element are configured to be coupled to/uncoupled from each other in order to form the first chamber enclosing the medical article.

10. The medical package of claim 1, wherein the stopper has predefined locations permitting the positioning of at least two fingers of a person in order to allow them to grip the stopper in the area of the predefined locations.

11. The medical package of claim 1, wherein at least one of the support element, the stopper, and the hollow protective cover has a part that is impermeable to bacteria but permeable to gases in order to permit gas sterilization of at least one of the first chamber and the second chamber.

12. The medical package of claim 11, wherein the part is formed by a membrane.

13. A method of unpacking a medical article contained in a medical package of a medical article as claimed in claim 1, wherein the method comprises:
    separating the hollow protective cover from the stopper by a first person in order to uncover the support element;
    gripping of the support element by a second person; and
    separation of the support element from the stopper held by the first person.

14. The method of unpacking as claimed in claim 13, wherein the method further comprises opening the first chamber defined by the support element in order to remove the medical article therefrom.

15. The method of unpacking as claimed in claim 13, wherein the method further comprises before the opening step, keeping the support element, which encloses the medical article, in a stand-by area pending the use of the medical article.

16. The method of unpacking as claimed in claim 13, wherein the method further comprises:
    separating the support structure from the hollow support tube, wherein the medical article is captive of the support element in a given orientation; and
    releasing the medical article from the support structure by pivoting the medical article.

17. The medical package of claim 1, wherein the support structure is configured to hold the medical article captive in a given orientation of the medical article and configured to release the medical article by pivoting the medical article.

18. The medical package of claim 1, wherein the medical article assembly is a sterilized one.

19. The medical package of claim 1, wherein the stopper is configured to be coupled to the support element of the medical article by engagement with partial overlap.

20. The medical package of claim 1, wherein the hollow protective cover is configured to be coupled to the stopper by engagement with partial overlap.

21. The medical package of claim 1, wherein the hollow protective cover has predefined locations permitting the positioning of at least two fingers of a person in order to allow them to grip the hollow protective cover, in the area of the predefined locations.

22. The medical package of claim 1, wherein the support structure is configured to hold the medical article so that the length of the medical article is able to be seen while the medical article is coupled to the support structure.

23. The medical package of claim 1, wherein the support structure comprises a valve having a deformable body presenting an orifice that is capable of switching, by deformation of the deformable body, from a retaining configuration in which the orifice of the valve presents a shape and/or dimensions making it possible to clamp the medical article, to a releasing configuration in which the orifice presents a shape and/or dimensions making it possible to release the medical article relative to the orifice of the valve.

24. The medical package of claim 23, wherein the orifice of the valve is oval shape.

25. A method of unpacking a medical article contained in a medical package of a medical article as claimed in claim 23, wherein the method comprises:
    a first person separating the cover from the stopper in such a manner as to uncover the support element;
    a second person distinct from the first person taking hold of the support element;
    separating the support element from the stopper while the stopper is being held by the first person;
    removing a support cap from the hollow support tube; and
    releasing medical article from the support structure by deforming the valve to make it pass from the retaining configuration to the releasing configuration.

26. The medical package of claim 1, wherein the support structure comprises a housing in which the medical article is held by resilient clamping or snap-fastening.

27. The medical package of claim 1, wherein the support structure comprises a stem-shaped portion having a top portion that is fitted with a coupler which suspends the medical article on the support structure.

28. The medical package of claim 1, wherein the support structure comprises a mandrel including a deformable elongate body along and inside which an orifice is formed for inserting the medical article and also including a bellows that surrounds the mandrel and that is capable of passing from a deployed position of the folds of the bellows, in which the bellows bears against the mandrel in such a manner as to clamp the insertion orifice around the medical article, to a compressed position of the folds of the bellows, in which the bellows does not press against the mandrel so as to enable the medical article to move relative to the insertion orifice for inserting the mandrel.

29. The medical package of claim 28, wherein the support structure includes at least two arms that are spaced apart from each other and that extend on either side and along the assembly formed of the mandrel and of the bellows.

30. A method of unpacking a medical article contained in a medical package of a medical article as claimed in claim 28, wherein the method comprises the following steps:
    a first person separating the cover from the stopper in such a manner as to uncover the support element;
    a second person distinct from the first person taking hold of the support element;
    separating the support element from the stopper while the stopper is being held by the first person;
    removing a support cap from the hollow support tube; and
    releasing the medical article from the support element by compressing the folds of the bellows, in which the bellows does not press against the mandrel, moving medical article relative to the insertion orifice.

* * * * *